US006969865B2

(12) United States Patent
Duchon et al.

(10) Patent No.: US 6,969,865 B2
(45) Date of Patent: Nov. 29, 2005

(54) SYSTEMS AND METHODS FOR DETECTION AND MEASUREMENT OF ELEMENTS IN A MEDIUM

(75) Inventors: Douglas Duchon, Chanhassen, MN (US); Steven Jester, Eden Prairie, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 145 days.

(21) Appl. No.: 10/076,837

(22) Filed: Feb. 14, 2002

(65) Prior Publication Data

US 2002/0145122 A1 Oct. 10, 2002

Related U.S. Application Data

(60) Provisional application No. 60/269,033, filed on Feb. 15, 2001.

(51) Int. Cl.[7] .......................... G01N 21/49; G01N 21/85
(52) U.S. Cl. .................. 250/573; 250/574; 250/214 R; 250/205; 356/436
(58) Field of Search .............................. 250/573, 574, 250/576, 214 R, 214 A, 205; 356/436, 437, 356/440; 73/19.1, 61.41, 61.43; 604/181, 604/186

(56) References Cited

U.S. PATENT DOCUMENTS

| | | | |
|---|---|---|---|
| 3,731,679 A | 5/1973 | Wilhelmson et al. | |
| 3,739,943 A | 6/1973 | Wilhelmson et al. | |
| 3,935,876 A | 2/1976 | Massie et al. | ............... 137/177 |
| 4,344,429 A | 8/1982 | Gupton et al. | ............... 128/214 |
| 4,512,764 A | 4/1985 | Wunsch | |
| 4,854,324 A | 8/1989 | Hirschman et al. | |
| 4,884,065 A * | 11/1989 | Crouse et al. | ............... 340/632 |
| 4,966,579 A | 10/1990 | Polaschegg | |
| 5,249,579 A | 10/1993 | Hobbs et al. | |
| 5,394,732 A * | 3/1995 | Johnson et al. | ............... 73/19.1 |
| 5,455,423 A * | 10/1995 | Mount et al. | ............... 250/343 |
| 5,494,036 A | 2/1996 | Uber, III et al. | |
| 5,515,851 A | 5/1996 | Goldstein | |
| 5,569,181 A | 10/1996 | Heilman et al. | |
| 5,621,205 A * | 4/1997 | Warner et al. | ............... 250/205 |
| 5,680,111 A | 10/1997 | Danby et al. | ............... 340/632 |
| 5,739,508 A | 4/1998 | Uber, III. | |
| 5,795,333 A | 8/1998 | Reilly et al. | |
| 5,806,519 A | 9/1998 | Evans, III et al. | |
| 5,808,203 A | 9/1998 | Nolan, Jr. et al. | |
| 5,840,026 A | 11/1998 | Uber, III et al. | |
| 5,843,037 A | 12/1998 | Uber, III. | |
| 5,873,861 A | 2/1999 | Hitchins et al. | |

(Continued)

FOREIGN PATENT DOCUMENTS

DE  37 20667  5/1989
WO  WO 00/15278  3/2000

*Primary Examiner*—Kevin Pyo
(74) *Attorney, Agent, or Firm*—Kramer Levin Naftalis & Frankel (57) ABSTRACT

Systems and associated methods are provided for improving detection and measurement of elements in a medium, particularly the measurement of gaseous bubbles in liquid medium, such as blood injected into a patient's body. The systems include a radiation emitter to emit radiation for traversing through a medium, and an analyzer subsystem to receive and to analyze the traversed radiation for presence and/or absence of gaseous elements in the medium. The methods include receiving at least one collection of data corresponding to at least one emitted radiation traversed through a medium, analyzing said collection of data for at least one predetermined condition; and generating a response upon detection of at least one predetermined condition.

48 Claims, 6 Drawing Sheets

U.S. PATENT DOCUMENTS

| | | |
|---|---|---|
| 5,885,216 A | 3/1999 | Evans, III et al. |
| 5,920,054 A | 7/1999 | Uber, III. |
| 5,947,935 A | 9/1999 | Rhinehart et al. |
| RE36,648 E | 4/2000 | Uber, III et al. |
| 6,096,011 A | 8/2000 | Trombley, III et al. |
| 6,149,627 A | 11/2000 | Uber, III. |
| 6,159,183 A | 12/2000 | Neer et al. ............ 604/189 |
| 6,197,000 B1 | 3/2001 | Reilly et al. |
| 6,306,117 B1 | 10/2001 | Uber, III. |
| 6,339,718 B1 | 1/2002 | Zatezalo et al. |
| RE37,602 E | 3/2002 | Uber, III et al. |
| 6,385,483 B1 | 5/2002 | Uber, III et al. |
| 6,440,107 B1 | 8/2002 | Trombley, III et al. |
| 6,442,418 B1 | 8/2002 | Evans, III et al. |
| 6,471,674 B1 | 10/2002 | Emig et al. |
| 6,520,930 B2 | 2/2003 | Critchlow et al. |
| 6,643,537 B1 | 11/2003 | Zatezalo et al. |

\* cited by examiner

SYSTEMS AND METHODS FOR DETECTION AND MEASUREMENT OF ELEMENTS IN A MEDIUM

CROSS REFERENCE TO RELATED APPLICATIONS

The present application claims priority of U.S. Provisional Application Ser. No. 60/269,033, filed Feb. 15, 2001, whose contents are fully incorporated herein by reference.

FIELD OF THE INVENTION

The present invention is generally directed to detectors. More particularly, the present invention relates to detectors used in medical devices for detecting the presence and/or lack of predetermined elements in a medium while increasing the precision in the dimensional measurements of the elements.

BACKGROUND OF THE INVENTION

Presently, many medical procedures with the goal of providing fluids to a patient's body through external tubing make use of detection mechanisms to monitor the presence of undesirable elements such as gaseous bubbles in the provided fluid. For example, one such commonly used procedure is for conducting dialysis. During dialysis, a patient's blood is generally circulated extracorporeally through an artificial kidney machine, such as a dialysis machine, where harmful and other undesirable elements in the blood are largely filtered from the blood. The filtered blood is then returned to the patient's body, generally through tubing connected directly to a blood vessel. The returned blood, however, may still contain undesirable elements, such as undissolved gaseous bubbles or columns of air that can be harmful if allowed to enter a patient's body. In order to prevent or minimize gaseous bubbles from entering the body, a detection device is commonly used to monitor the blood for the gaseous bubbles prior to the bubbles entering the patient's body. An example of one such air-bubble detector is set forth in U.S. Pat. No. 5,583,280, the disclosure of which is herein incorporated by reference.

Currently, ultrasonic air bubble detectors are used for monitoring blood for gaseous bubbles and other undesirable elements. The details of one such ultrasonic air bubble detector are set forth in U.S. Pat. No. 5,394,732 to Johnson et al, the disclosure of which is herein incorporated by reference.

Conventional ultrasonic air bubble detectors generally transmit an ultrasonic wave from a transmitter through the tubing containing the flowing blood. An ultrasonic wave receptor/detector collects the transmitted wave at the opposite side of the tubing and the waveform is then translated into a signal and analyzed. The analysis generally involves a study of the changes in the ultrasonic waveform characteristics, such as attenuation, resulting from passage through a fluid medium, such as blood. These changes are then compared to predetermined settings indicating the presence of gaseous bubbles in the blood. Other changes in the blood affecting propagation of the ultrasonic wave, such as increased or decreased blood density, are also analyzed and fed back to the transmitter. The transmitter then re-calibrates various waveform parameters, such as intensity and/or frequency, to account for any changes in the blood, thus enabling the detector to continuously detect gaseous bubbles.

In addition to fluid changes, other factors may also affect and/or compromise bubble detection capabilities using ultrasound. For example, it is generally well known that sound waves are susceptible to noise, both ambient and internal. As a result, there exists the potential that any noise detected by the receiver, together with the waveform signal, may cause an erroneous bubble-detection reading. In addition, a sound wave's relatively large wavelength may limit a detector's degree of precision in detecting and/or measuring bubble sizes. In particular, small bubbles of air, for example on the order of several micro-liters, may flow through the tubing undetected by the detector and enter the patient's circulatory system. Such an occurrence would obviously be very harmful, and likely fatal, to the patient.

Although presently available bubble detection devices are well accepted by the medical profession, it is desirable to have a detector that can further minimize and better detect the number of bubbles that may be entering the body of a patient. In particular, it is desirable to have a detector that can detect smaller bubbles of air and with greater degree of precision, while providing for faster recalibration of the detector in the event of sudden changes in the fluid medium.

SUMMARY OF THE INVENTION

In view of the foregoing, it is the object of the present invention to provide a bubble detection system that addresses the obstacles and disadvantages associated with current bubble detectors.

A further object of the present invention is to provide a bubble detector system that can accommodate a variety of tubing designs and fluids having various volumes, concentrations, viscosities, etc.

A further object of the present invention is to provide a cost-effective system with reliable and repeatable detection capabilities, thereby eliminating false air-detect readings/signals.

The present invention attempts to address these objects and other objects not specifically enumerated herein through the use of a detector system that includes at least one radiation emitter subsystem to emit at least one radiation emission for traversing through a medium and at least one analyzer subsystem to receive and analyze the traversed radiation for presence and/or absence of gaseous elements in the medium. The system may detect gaseous elements in both stationary and flowing fluid.

Another embodiment the present invention contemplates a method for analyzing data to determine presence and/or absence of predetermined conditions in a medium. The method includes receiving at least one collection of data corresponding to at least one emitted radiation traversed through a medium, analyzing the collection of data for at least one predetermined condition and generating a response upon detection of at least one predetermined condition.

Another embodiment of the present invention contemplates a method for sensing as used in a detector. The method includes emitting at least one radiation emission traversing through a medium, receiving and analyzing the traversed radiation for presence and/or absence of gaseous elements in the medium and generating data based on the analysis.

In one embodiment of the present invention, a graphical user interface having internal power, input panels with preset command and display of status lines is used to better aid the user with the operations of the present invention. The interface may communicate with the present invention in either parallel or serial mode. In addition, multiple emitters may also be used in combination to increase the accuracy of the detection and/or calibration process.

This brief summary has been provided so that the nature of the invention may be understood quickly. A more complete understanding of the invention can be obtained by reference to the following detailed description and drawings.

BRIEF DESCRIPTION OF THE DRAWINGS

Other features and advantages of the present invention will be seen as the following description of particular embodiments progresses in conjunction with the drawings, in which.

DETAILED DESCRIPTION OF THE INVENTION

The present invention is directed to improving the detection capability and detection time by which the presence and/or absence of predetermined elements is detected in a medium while also increasing the precision in the dimensional measurements of the predetermined elements. The present invention may be utilized with various systems. Examples of systems included within the scope of the present invention include, but are not limited to, the systems disclosed in U.S. Pat. No. 6,221,045, U.S. Pat. No. 6,004, 292, U.S. Pat. No. 5,988,587, U.S. Pat. No. 4,650,465, U.S. Pat. No. 5,451,211, U.S. Pat. No. 5,456,670, U.S. Pat. No. 4,695,271, U.S. Pat. No. 5,865,805, U.S. Pat. No. 5,925,022, U.S. Pat. No. 5,899,885, U.S. Pat. No. 6,042,565, U.S. Pat. No. 6,063,052, U.S. Pat. No. 6,090,064, U.S. Pat. No. 6,149,627, the disclosures of which are hereby incorporated by reference in their entirety into the present application.

Although the present invention is described with reference to radiation, the term radiation, as used herein, includes, but is not limited to, light, ultrasound, electromagnetic and other energy forms known in the art.

Figure 1:
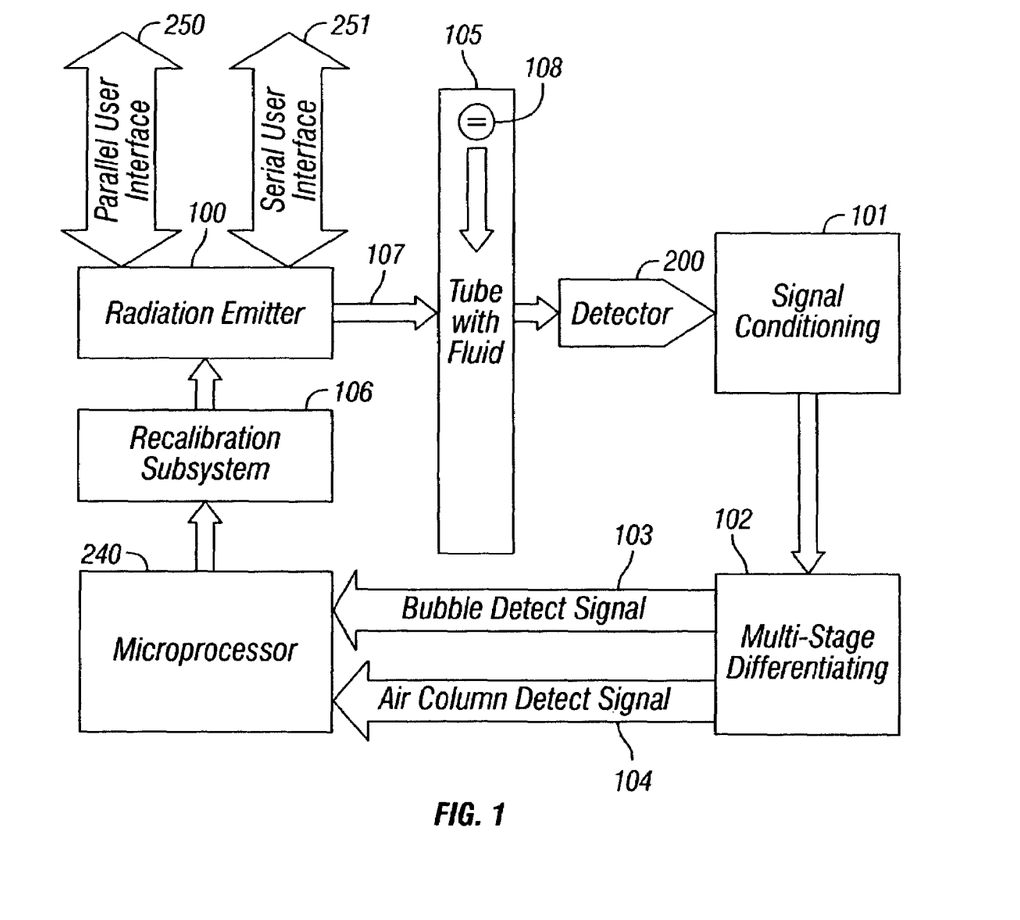
FIG. 1 illustrates one embodiment of the overall system architecture of the present invention.

FIG. 1 illustrates the overall system architecture of one embodiment of the present invention. The system includes a radiation emitter subsystem 100, detector subsystem 200, signal conditioning subsystem 101, multi-stage differentiating subsystem 102, and recalibration subsystem 106. This non-invasive system does not contact fluid or require a break in tubing to detect the presence of air.

As illustrated in FIG. 1, the radiation emitter (or transmitter) subsystem 100 emits a radiation waveform 107 that traverses through tubing 105 containing a fluid medium such as blood. The radiation waveform 107 is received by receiver or detector 200, converted into an electro-optical signal and forwarded to the signal conditioning subsystem 101. Although the emitter 100 and detector 200 illustrated in FIG. 1 are in linear alignment with each other, other configurations including, but not limited to, angled alignment or parallel alignment, are also included within the scope of the present invention. The signal conditioning subsystem 101 filters out undesirable components of the signal, such as noise and ambient light, before forwarding the signal to the multistage differentiating subsystem 102.

The multi-stage differentiating subsystem 102 subsequently determines whether any undesirable elements 108, such as undissolved gaseous bubbles or columns of air, exist in the fluid medium. Other determinations, such as presence of tubing, absence of tubing, empty tubing, fluid filled tubing, stagnant air bubbles and/or sensor door state, may also be performed. The results of these determinations are outputted, such as in the form of a bubble detect signal 103 or a column (e.g., air column) detect signal 104, to microprocessor 240. If the microprocessor and its algorithms 240 detect the presence of any undesirable elements 108, flow of operation may be interrupted and/or warnings to the user may be generated. The results of these determinations are also forwarded to the recalibration subsystem 106 in the form of a feedback signal. Based on the feedback data, the recalibration subsystem 106 can then recalibrate the radiation emitter subsystem 100 to a desired setting by altering the characteristics of the emitted radiation waveform, such as changing the intensity and/or frequency of the waveform. The recalibration is required for numerous reasons including: temperature drift, LED degradation, mechanical alignment (including tubing position, tubing clarity, etc.) and change in fluid medium (e.g., blood (opaque) to saline (clear)).

In one embodiment of the present invention, a user interface, such as a parallel user interface 250 or serial user interface 251, can be coupled to the system for ease of use by a user. In addition, the system may also be configured for low power, possible battery operation, and small over-all size.

Figure 2:
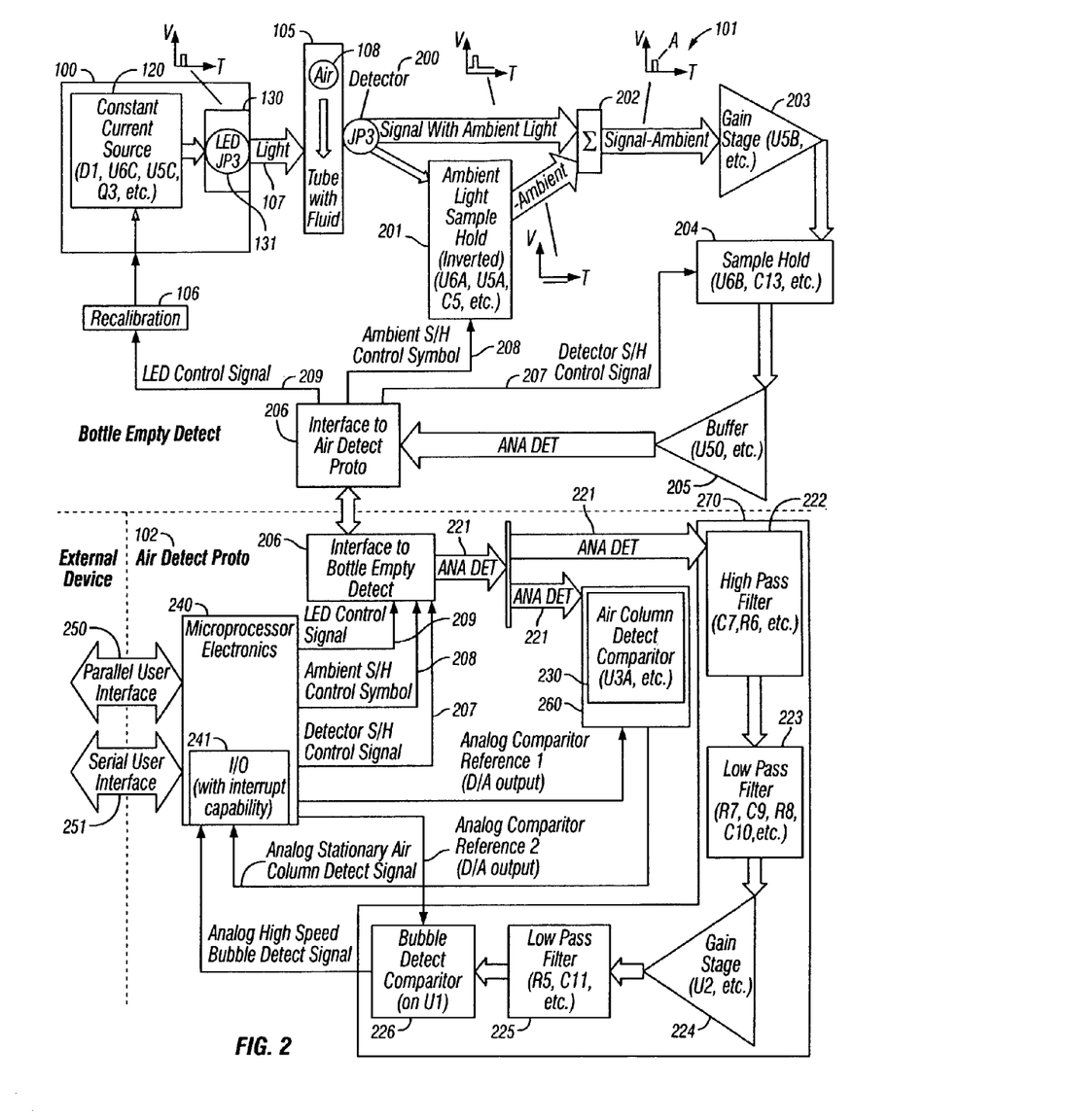
FIG. 2 illustrates in greater detail the flow of the operations of one embodiment of the present invention.
Figure 3:
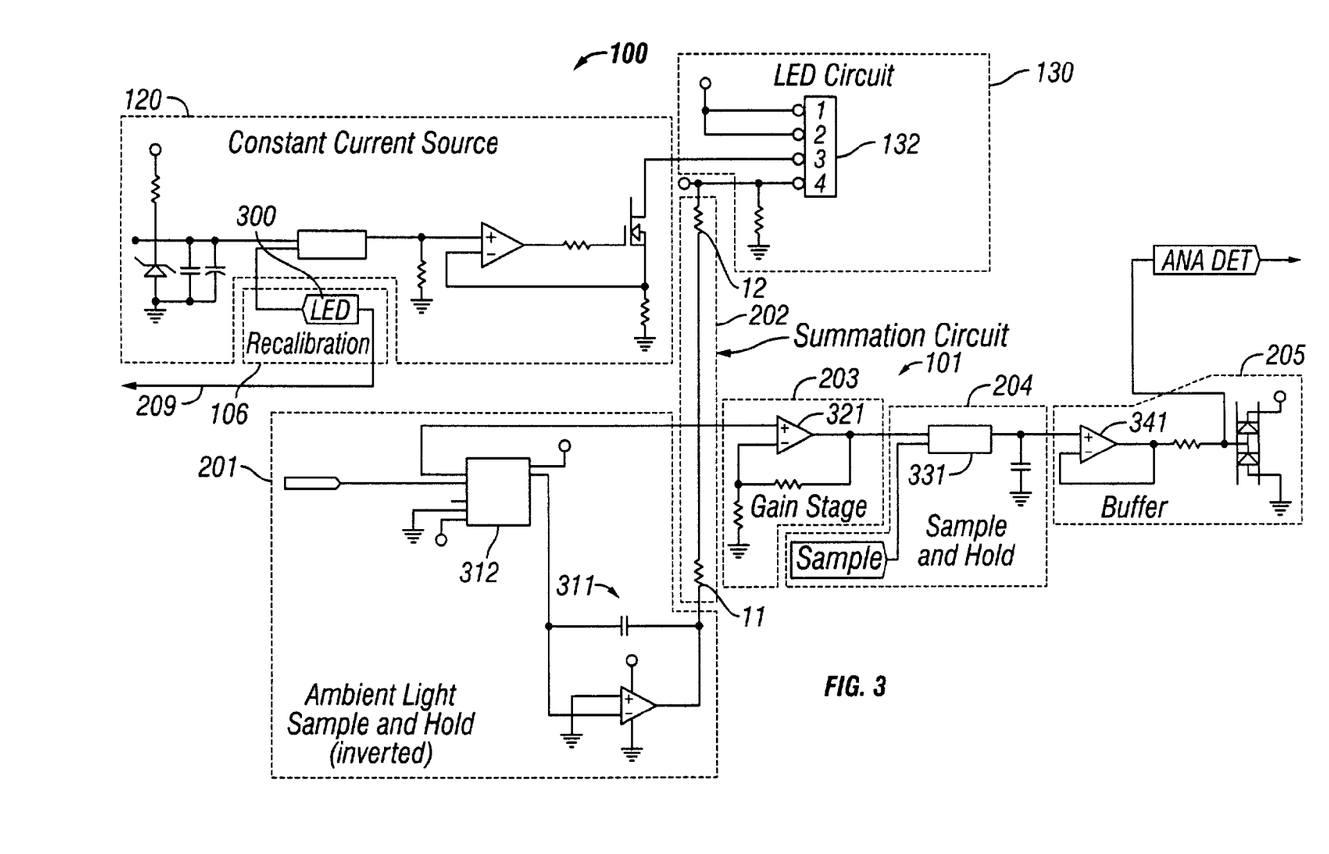
FIG. 3 is one embodiment of a circuit diagram of one subsystem of the present invention illustrated in FIG. 2.
Figure 4:
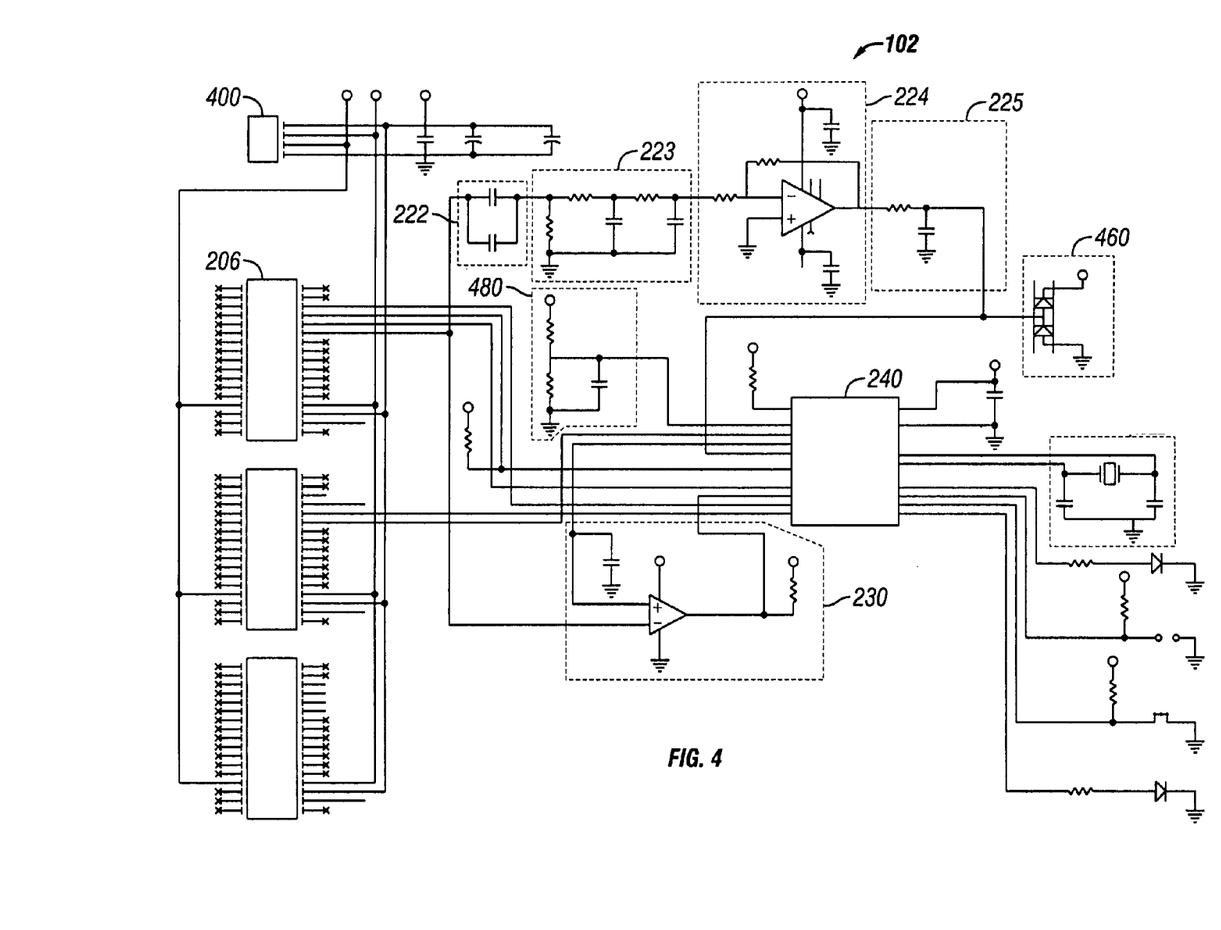
FIG. 4 is one embodiment of a circuit diagram of another subsystem of the present invention illustrated in FIG. 2.

FIGS. 2, 3 and 4 illustrate in greater detail the flow of operations (FIG. 2) and associated circuitry (FIGS. 3 and 4) of the present invention.

As illustrated in FIG. 2, the radiation emitter subsystem 100 includes a constant current source subsystem 120 and a light emitting diode subsystem 130. The programmable adjustable constant current source subsystem 120 controls the flow and characteristics of the waveform to be generated and emitted by the light emitting diode subsystem 130. The light emitting diode subsystem 130 includes a light emitting diode (LED) 131 and a LED circuit 132. The LED circuit 132 (shown in FIG. 3) receives control-instructions from the light emitting diode subsystem 130 and accordingly activates the LED 131 to emit the desired radiation waveform 107. As illustrated in the circuit diagram in FIG. 3 and discussed in greater detail below, the radiation waveform 107 emitted by the LED 131 can be recalibrated by the recalibration subsystem 106.

Referring more particularly to FIG. 2, the radiation waveform 107 emitted by the LED 131 traverses through tubing 105 containing a fluid medium, such as blood, and is received by detector 200. The detector 200 converts the received waveform into an electro-optical signal for forwarding to the signal conditioning subsystem 101. In an exemplary embodiment illustrated in the circuit diagram of FIG. 3, the LED circuit 132 can be used to both send signals to the LED 131, such as from pins 1 and 3, and receive subsequent signals from detector 200, such as in pin 2, for forwarding to the signal conditioning subsystem 101, such as from pin 4. In an exemplary embodiment of the present invention, multiple radiation waveforms 107 emitted from one or multiple radiation emitter subsystems 100 stationed at the same or axially different angles to the fluid medium may be used. Each waveform can then be analyzed and matched against the results of the other to increase the accuracy and precision of the subsequent analysis.

Returning to FIG. 2, the signal conditioning subsystem 101 includes ambient-light sample-and-hold (ALSH) subsystem 201, summation circuit subsystem 202, gain stage amplifier subsystem 203, a sample and hold subsystem 204, buffer subsystem 205 and interface unit 206.

Once the waveform 107 is converted into an electro-optical signal, it is forwarded to the signal conditioning subsystem 101 where it is received by both the ALSH subsystem 201 and summation circuit subsystem 202. The two subsystems 201 and 202 effectively operate together to remove noise, such as ambient light components, from the received waveform 107. For example, when traversing through tubing 105 containing a fluid medium such as blood and/or outside atmosphere, ambient light can be undesirably mixed into the emitted radiation prior to reception by detector 200 and, therefore, has to be removed prior to the signal analysis stage. To this end, the ALSH subsystem 201 periodically samples the signal to separate and hold the ambient light components from the signal. The sampled ambient light components are then forwarded to the summation circuit subsystem 202 where the separated ambient light components are continuously subtracted from the received signal, thereby generating the desired waveform 107 (i.e., free from noise) from the received signal.

FIG. 3 illustrates an exemplary embodiment of the ALSH subsystem 201 circuitry, along with the summation circuit subsystem 202 which includes a pair of resistors 11,12. As shown, the ALSH subsystem 201 circuitry includes the sample-and-hold circuit 312 and the inverted amplifier circuit 311. The ambient light components of the signal are extracted in the form of a voltage differential and outputted to the inverted amplifier circuit 311 which then converts this voltage into a negative voltage. The negative voltage is then outputted to the summation circuit subsystem 202 and added to the received signal, thus effectively subtracting the ambient light from the received signal.

Returning to FIG. 2, the waveform signal is then amplified by the gain stage amplifier subsystem 203 and forwarded to the sample-and-hold subsystem 204. A sample of the waveform signal is periodically collected by the sample-and-hold subsystem 204 according to a desired, predetermined time interval, resulting in faster processing of the waveform signal by the recalibration subsystem 106 via software analysis. The sampled signal is collected with sufficient periodicity so that the interim changes in the waveform signal become negligible. One advantage of the foregoing feature of the present invention is improved analysis response time due to a reduction in the amount of data to be processed. In addition, it should also be noted that the sample-and-hold subsystem 204, while desirable, is not essential to the overall operation of the present invention.

Still referring to FIG. 2, the waveform signal is then passed through a protective buffer subsystem 205 and into the interface unit 206, which forwards the signal to another interface unit 206 at the multi-stage differentiating subsystem 102. In one embodiment of the present invention wherein multiple radiation waveforms/signals 107 are emitted from one or multiple radiation emitter subsystems, multiple interface units 206 may also be utilized in the signal conditioning subsystem 101 and/or differentiating subsystem 102 for faster transmission and reception of the multiple signals.

As illustrated FIG. 2, the differentiating subsystem 102 includes interface unit 206, gas-column detector (GCD) subsystem 260, gas-bubble detector (GBD) subsystem 270, and microprocessor 240. The GBD subsystem 270 further includes a high-pass filter 222, a first low pass filter 223, gain stage amplifier 224, a second low pass filter 225 and gas-bubble detect (GBD) comparator subsystem 226. The GCD subsystem 260 includes gas-column detector comparator subsystem 230.

Referring more particularly to FIG. 2, the waveform signal transmitted from interface 206 in signal conditioning subsystem 101 is received at interface 206 in multistage differentiating subsystem 102 and forwarded to GCD subsystem 260 and GBD subsystem 270. As described below in greater detail, the two subsystems 260 and 270 analyze the waveform signal to determine the presence and/or absence of any gaseous bubbles or columns in the fluid medium.

In entering the GBD subsystem 270, the waveform signal is passed through a high-pass filter 222 to minimize the noise in the signal. Next, the waveform signal is passed through a low-pass filter 223 to filter out changes in the signal considered too rapid in passage to be caused by gas bubbles, such as signal changes in excess of 20 megahertz. The two filters are placed in tandem to effectuate a band-pass filter that allows for passage of a signal having minimal low or high frequencies. FIG. 4 illustrates the circuitry details of one embodiment of a high-pass filter 222 that includes a pair of capacitors placed in parallel and a low-pass filter 223 that includes a pair of resistors placed serially and electrically connecting a pair of capacitors placed in parallel.

Returning to FIG. 2, the filtered signal is then amplified by the gain stage amplifier 224 and passed through a second low-pass filter 225 to further minimize signal noise.

Next, the signal is fed to the GBD comparator subsystem 226. The GBD comparator subsystem 226 analyzes the received signal by comparing the data to adjustable, predetermined signals that indicate the presence and/or absence of gaseous bubbles in the medium and outputs a comparison result to the microprocessor 240. In one embodiment of the present invention, the presence of a bubble in contrast or saline injected at, for example, more than 800 psi in a conventional 0.078-inch-diameter, 95-durometer, high-pressure tubing, is predetermined as a less than 10 micro-liter fluid displacement resulting in a voltage change greater than or equal to the programmable reference voltage. In this embodiment, the GBD comparator subsystem 226 compares the signal with the adjustable predetermined signal of a 20 milli-volt reference voltage provided by the reference voltage subsystem 480 to determine the presence and/or absence of gaseous bubbles in the medium and outputs a comparison result to the microprocessor 240.

FIG. 4 illustrates the circuitry details of an exemplary embodiment of the present invention's gain stage amplifier 224, the second low-pass filter 225, and the voltage diode protector 460 guarding against excessive voltage from entering the microprocessor 240. In an exemplary embodiment as illustrated in FIG. 4, the GBD comparator subsystem 226 is housed within microprocessor 240. The reference voltage subsystem 480 generated the adjustable predetermined signals, such as, for example, 20 millivolts, for the GBD comparitor subsystems 226.

In entering the GCD subsystem 260, the waveform signal is passed through the gas-column detector comparator subsystem 230. The gas-column detector comparator subsystem 230 analyzes the received signal by applying the appropriate algorithm for the fluid type in the application. The bubble/column determination is programmable within the microprocessor 240 and, in one embodiment, may be a set reference of 20 milli-volts. In one embodiment of the present invention, the presence of a gas column in fluid injected at, for example, more than 800 psi in a conventional 0.078-inch-diameter, 95-durometer, high-pressure tubing is predetermined as a 10 micro-liter or more fluid displacement resulting in a voltage change of equal to or exceeding 20 milli-volts. In this embodiment, the gas-column detector comparator subsystem 230 compares the signal with the adjustable predetermined signal of a 20 milli-volt reference voltage, provided by reference voltage subsystem 480, to determine the presence and/or absence of gaseous columns in the medium and outputs a comparison result to the microprocessor 240.

Figure 5A:
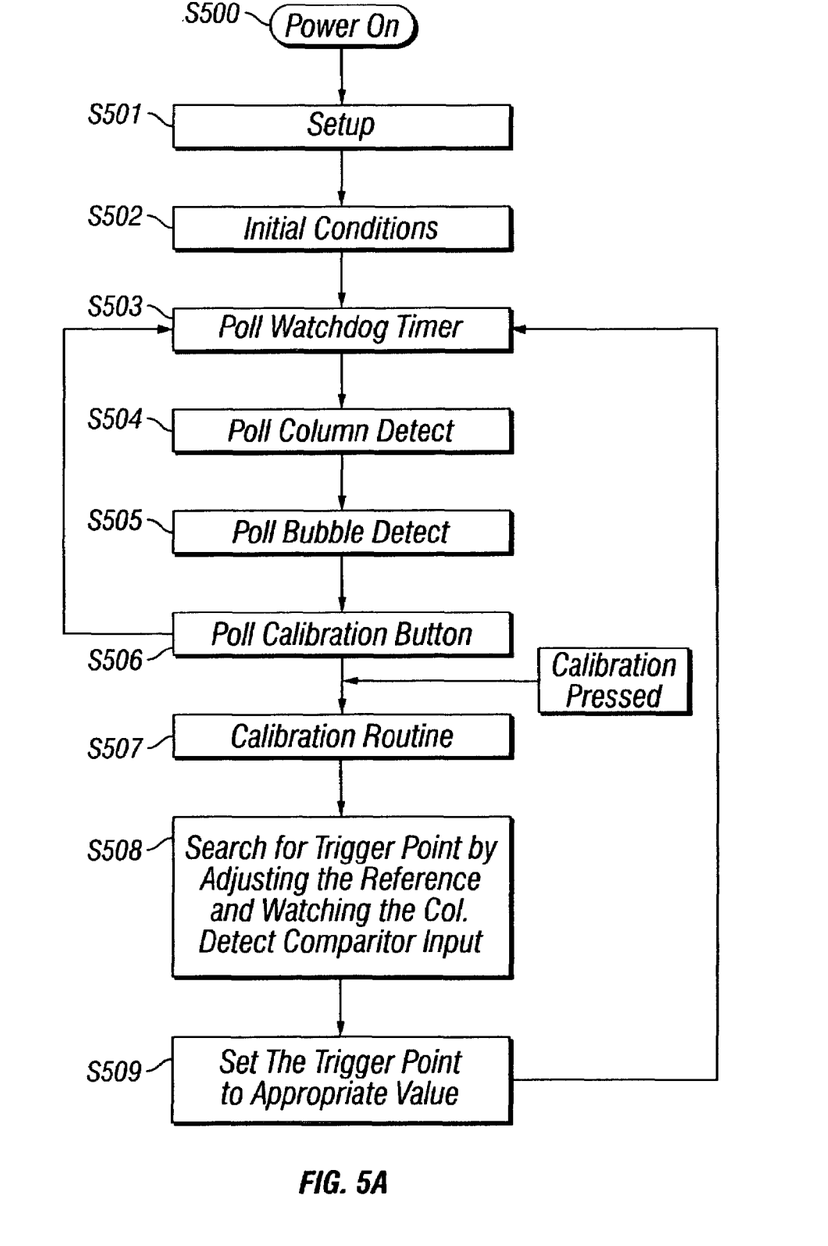
FIG. 5A is one embodiment of a flow chart of the operations of a subsystem of the present invention illustrated in FIG. 2.
Figure 5B:
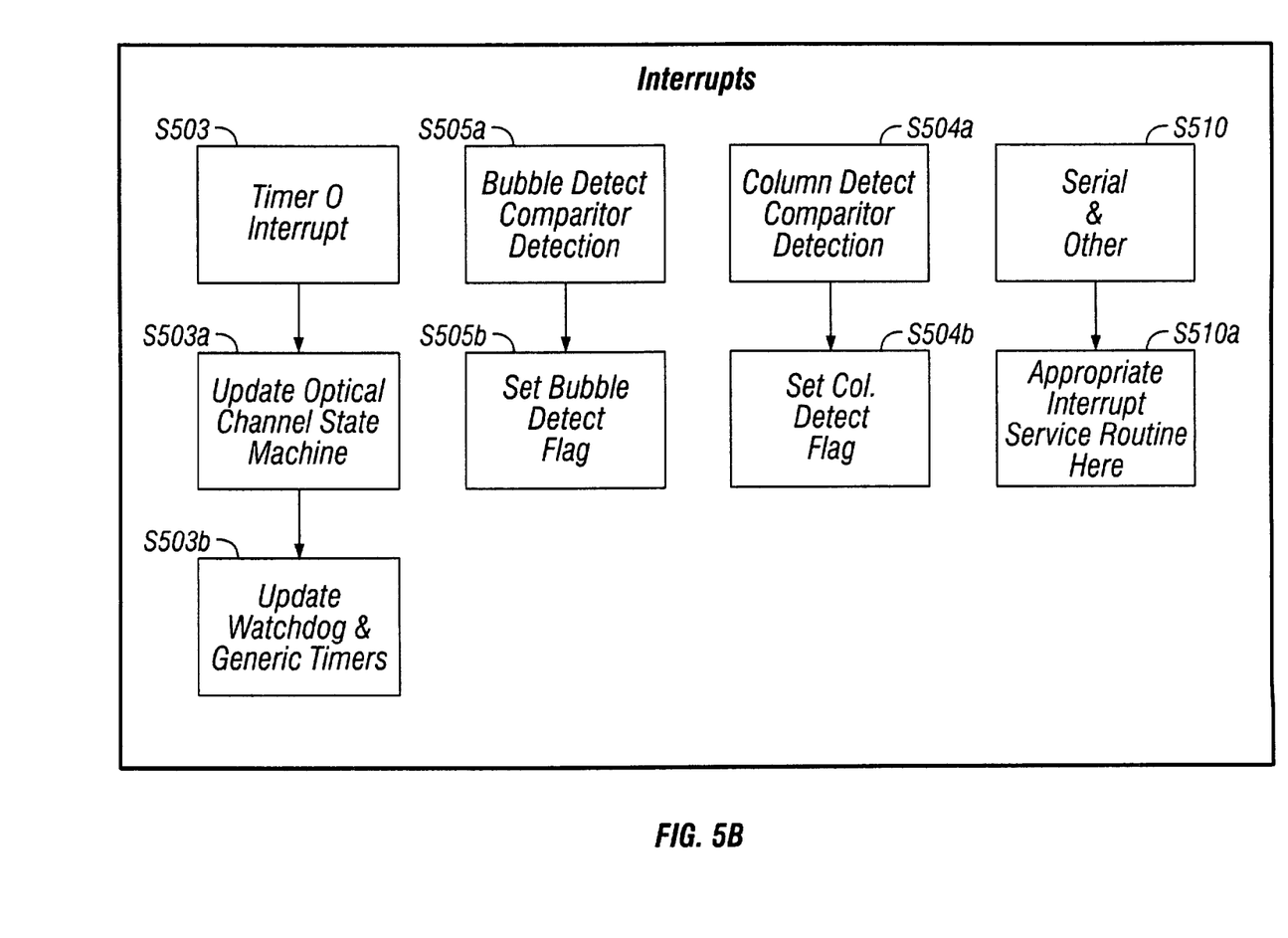
FIG. 5B is another embodiment of a flow chart of the operations of a subsystem of the present invention as illustrated in FIG. 2.

The microprocessor 240, which receives the comparison results from both GCD subsystem 260 and GBD subsystem 270, is an interrupt-driven microprocessor. Flowcharts of the various operations or processes performed by the microprocessor 240 are illustrated in FIGS. 5A and 5B. After initial power-up S500 and execution of internal operating instructions S501, initial predetermined conditions for the detection of various interrupts are accessed for future comparisons.

In addition, the microprocessor 240 checks to determine whether a predetermined clock cycle has expired S503. Expiration of clock cycle S503 prior to completion of a task prompts the microprocessor 240 to do any or all of the following: interrupt the flow of operations, issue recalibration instructions to the recalibration subsystem 106, issue a warning to the user, and/or proceed with the next task in the task queue. In addition, as illustrated in FIG. 5B, setting the timer to zero S503 may prompt the microprocessor 240 to update the state of optical channels S503a and reset the watchdog and generic timers S503b.

The results from the GCD comparator subsystem 226 are then analyzed S504. Detection of the presence of a gaseous column S504a in the tubing results in the triggering/setting of a column-detect flag S504b. The microprocessor polls the column detect results S504 for the presence of any flags. If any gaseous columns are found, then the microprocessor executes any or all of the following: interrupt the flow of operations, issue recalibration instructions to the recalibration subsystem 106, and/or issue a warning to the user.

The results from the GBD comparator subsystem 226 are also analyzed S505 by the microprocessor 240. Detection of the presence of a gaseous bubble S505a in the tubing results in the triggering/setting of a bubble-detect flag S505b. The microprocessor polls the bubble detect results S505 for the presence of any flags. If any gaseous bubbles are found, then the microprocessor executes any or all of the following: interrupt the flow of operations, issue recalibration instructions to the recalibration subsystem 106, and/or issue a warning to the user.

In addition, the microprocessor 240 checks to see whether a LED calibration button was pressed S506. The LED calibration button is used when a new LED 131 replaces an older unit or when the system is turned off and on. In the event of a new LED 131 replacing an older unit, recalibration is necessary since each manufactured LED 131 has an inherently different emitting spectrum or frequency and, thereby, voltage. A determination of such voltage is necessary to make an accurate reading of the resulting waveform signal for detection of gaseous bubbles and columns. LED calibration S507 is initiated by repeatedly adjusting the input voltage in the LED S508 until the emission voltage is found. Thereafter, the new emission voltage is used in place of the older one S509. In one embodiment of the present invention, the new emission voltage is stored in a memory medium such as an EEPROM so that the calibration routine does not have to be repeated when the system is turned off and on.

Other predetermined events or conditions S510 may also be monitored and analyzed by the microprocessor 240. As such, if a predetermined event is detected S510, then the microprocessor 240 may execute any or all of the following: interrupt the flow of operations, issue recalibration instructions to the recalibration subsystem 106, and/or issue a warning to the user. Examples of such events include, but are not limited to, presence of tubing, absence of tubing, empty tubing, fluid filled tubing, stagnant air bubbles and/or sensor door state.

In addition, if the microprocessor 240 determines that a recalibration of the radiation emitter subsystem 100 is required, then the microprocessor 240 issues recalibration instructions in the form of a LED control signal 209. In one embodiment of the present invention as illustrated in FIG. 2, the LED control signal 209 is sent to the interface unit 206 of the multi-stage differentiating subsystem 102, is received at interface 206 in the signal conditioning subsystem 101 and forwarded to the recalibration subsystem 106.

The recalibration subsystem 106 includes the LED control unit 300 which, in turn, updates the controlling constant current source subsystem 120 of the recalibration changes based on LED control signal 209 received from the multi-stage filtering subsystem 102. In one embodiment of the present invention, the recalibration instruction may, for example, include commands for the constant current source subsystem 120 to adjust the frequency and/or intensity of the emitted radiation from the LED unit 130.

In addition, the microprocessor 240 may similarly send operational instructions, such as actuation timing, and/or data to the ALSH subsystem 210 using ALSH control signal 208, or to sample-and-hold subsystem 204 using detector sample-and-hold signal 207.

In general, based on the foregoing, the system of the present invention may detect a small bolus of air (i.e., on the order of several microliters measured at ambient pressure) when injected at 800–11,000 psi pressure with a flow rate from 0 ml/sec to 50 ml/sec in a 0.078 inch to 0.088 inch inner diameter, 95 durometer, high pressure tubing. As previously described, the system includes an auto-subtraction feature whereby ambient light and high artificial noise are subtracted or removed to prevent signal distortion and/or erroneous results. In addition, the auto-calibration or self-calibration mode of the system of the present invention zeros out effects of mechanical alignment (such as those affecting refraction), transceiver efficiency, tubing/fluid transmittance changes (e.g., tubing material change, fluid viscosity change), tubing/fluid reflectivity changes, tubing/fluid absorption changes, fluid color and other degenerating effects. To further ensure optimum performance, the system also includes a self-test mode that may be used to verify that the various components of the system (e.g., microprocessor, transmitter, receiver, cabling, etc.) are functioning properly.

Although the system has been described with reference to particular features and components, other designs and configurations including, but not limited to, more accurate detection of bubble speed and size, quantified detection of bubble speed and size, additional system-compatible media and fluid types, media and fluid type detection, fail safe operation, and component/sensor self-test, are also included within the scope of the present invention.

It is noted that the foregoing different embodiments of the present invention were illustrated separately at times for the purpose of brevity and reader convenience. As such, any process or system using one or more of the disclosed embodiments, including embodiments not specifically disclosed herein, is also included within the scope of the claimed invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for use in a detector, said system comprising:
   at least one radiation emitter subsystem to emit at least one radiation emission for traversing through a medium;
   at least one analyzer subsystem to receive and to analyze said radiation for presence and/or absence of gaseous elements in said medium;
   a filtering subsystem to separate the emitted radiation from ambient radiation in said received radiation; at least one ambient-light-sample-and-hold subsystem to receive said received radiation in form of an electrical and/or optical signal and to determine ambient light components in said signal;
   at least one summation subsystem to receive said received radiation in the form of a representative electrical signal, to receive ambient light components in said signal from said ambient-light-sample-and-hold subsystem and to subtract said components from said signal; and
   at least one amplifier for amplifying said subtracted signal.

2. The system of claim 1, wherein said radiation emitter subsystem is a calibration-driven emitter subsystem to alter intensity and/or frequency of said emitted radiation.

3. The system of claim 2, further comprising:
   a calibration-driver subsystem to receive analysis data from said analyzer subsystem and to recalibrate said calibration-driven emitter subsystem based on said analysis data.

4. The system of claim 1, said analyzer subsystem further comprising:
   a differentiator subsystem to receive said separated emitted radiation, to determine presence and/or absence of gaseous elements in said medium and to differentiate between said gaseous elements.

5. The system of claim 1, wherein said analyzer subsystem further analyzes said radiation for presence and/or absence of a tubing and/or state of a sensor door mechanism.

6. The system of claim 4, wherein said differentiator subsystem differentiates between said gaseous elements based on size of their resultant gaseous bubbles.

7. The system of claim 6, wherein said differentiator subsystem differentiates between said gaseous elements based on a predetermined routine.

8. The system of claim 4, said differentiator subsystem further comprising:
   a gas-bubble detect subsystem to detect and report presence and/or absence of gaseous bubbles in said medium;
   a gas-column detect subsystem to detect and report presence and/or absence of gaseous columns in said medium; and
   a processor subsystem to receive and analyze said reports from said detect subsystems.

9. The system of claim 8, said processor subsystem to issue calibration instructions based on said analyzed reports to a calibration driver subsystem.

10. The system of claim 8, said gas-bubble detect subsystem further comprising:
    at least one band-pass filter to receive said received radiation in the form of a representative electrical signal and to minimize undesirable components of said signal;
    at least one inverting amplifier to receive said minimized signal from said band-pass filter, to generate a positive amplified signal based on said received minimized signal and to output said amplified signal;
    an adjustable signal generator subsystem to generate an adjustable predetermined signal; and
    a bubble-detect comparator subsystem to receive said outputted amplified signal, to compare said signal with said outputted amplified predetermined signal to determine presence and/or absence of gas bubbles in medium and to output a comparison result to said processor subsystem.

11. The system of claim 10, said band-pass filter further comprising:
    a high-pass filter to reduce noise component in said signal, said high-pass filter outputting to a low-pass filter to further minimize undesirable components of said signal.

12. The system of claim 8, said gas-column detect subsystem further comprising:
    an adjustable signal generator subsystem to generate an adjustable predetermined signal; and
    a gas-column comparator subsystem to receive said received radiation in the form of a representative electrical signal, to compare said signal with said predetermined signal to determine presence and/or absence of gaseous columns in the medium, and to output a comparison result to said processor subsystem.

13. The system of claim 1, said filtering subsystem further comprising: at least one sampler-sample-and-hold subsystem to periodically sample said subtracted signal.

14. The system of claim 8, said processor subsystem further comprising: at least one interrupt-driven subsystem to interrupt flow of operation of said system and to provide a warning upon detection of a predetermined undesirable condition in said reports.

15. The system of claim 15, wherein said predetermined undesirable condition is indication of presence and/or absence of at least one gaseous bubble and/or gaseous columns in said reports.

16. The system of claim 15, wherein said predetermined undesirable condition is a time-out interrupt or a malfunction within the system.

17. The system of claim 1, wherein said medium is a substantially liquid medium.

18. The system of claim 1, wherein said radiation emitter subsystem emits radiation in frequencies of visible light.

19. A method for analyzing data to determine presence and/or absence of predetermined conditions in a medium, said method comprising:
    receiving at least one collection of data corresponding to at least one emitted radiation traversed through a medium;
    analyzing said collection of data for at least one predetermined condition wherein said analyzing includes separating said emitted radiation from ambient radiation in said received collection of data; and generating a response upon detection of at least one said predetermined condition wherein said response includes interrupting flow of operations and/or providing a warning, wherein said separating includes receiving said collection of data in the form of a representative electrical signal in at least one ambient radiation sample-and-hold circuit for determining an ambient radiation component in said collection of data;

receiving said collection of data in the form of a representative electrical signal in at least one summation circuit, receiving said ambient light component in said signal from said ambient-light-sample-and-hold circuit and subtracting said ambient light component from said signal; and amplifying said subtracted signal utilizing at least one amplifier.

20. The method of claim 19, wherein said radiation is emitted from a calibration-driven emitter subsystem and wherein said response includes issuing of re-calibration instructions to said calibration-driven emitter subsystem.

21. The method of claim 20, wherein said predetermined condition is presence and/or absence of at least one gaseous bubble in said medium.

22. The method of claim 20, wherein said predetermined condition is presence and/or absence of at least one gaseous column in said medium.

23. The method of claim 20, wherein said predetermined condition is a predetermined condition of a timer unit.

24. The method of claim 20, wherein said predetermined condition is a execution of a calibration subroutine.

25. The method of claim 24, said execution of a calibration subroutine further comprising:

adjusting a reference voltage and matching said reference voltage against a voltage reference point for a light-emitting diode; and repeating said adjusting until said reference voltage matches the voltage reference point of said light-emitting diode.

26. The method of claim 25, said execution of a calibration subroutine further comprising:

resuming the flow of operations upon said matching of the reference voltage to said voltage reference point.

27. The method of claim 25, said execution of a calibration subroutine further comprising:

storing said matched reference voltage in a memory medium.

28. The method of claim 20, wherein said predetermined condition is presence and/or absence of a tubing.

29. The method of claim 20, wherein said predetermined condition is a predetermined state of a sensor door mechanism.

30. A method for sensing used in a detector, said method comprising:

emitting at least one radiation emission, said radiation traversing through a medium;

receiving and analyzing said traversed radiation for presence and/or absence of gaseous elements in said medium, wherein said analyzing includes separating said emitted radiation from ambient radiation in said received radiation; and generating analysis data based on said analyzing, wherein said separating includes:

receiving said received radiation in the form of a representative electrical signal in at least one ambient-light-sample-and-hold circuit for determining an ambient light component in said signal;

receiving said received radiation in the form of a representative electrical signal in at least one summation circuit, receiving ambient light component in said signal from said ambient-light-sample-and-hold circuit and subtracting said ambient light component from said signal; and amplifying said subtracted signal utilizing at least one amplifier.

31. The method of claim 30, wherein said emitting is calibration-driven for altering intensity and/or frequency of said emitted radiation.

32. The method of claim 31, further comprising:

receiving said analyzed data and re-calibrating said calibration-driven emitting based on said analyzed data.

33. The method of claim 30, said analyzing further comprising:

receiving said separated emitted radiation and determining presence and/or absence of gaseous elements in said medium; and differentiating between said gaseous elements.

34. The method of claim 30, said analyzing further comprising:

analyzing said radiation for presence and/or absence of a tubing and/or state of a sensor door mechanism.

35. The method of claim 33, wherein said differentiating between said gaseous elements is based on size of their resultant gaseous bubbles.

36. The method of claim 35, wherein said differentiating between said gaseous elements is based on a predetermined routine.

37. The method of claim 33, differentiating further comprising:

detecting presence and/or absence of gaseous bubbles in medium;

detecting presence and/or absence of gaseous columns in the medium; and analyzing said detecting and generating at least one analysis report.

38. The method of claim 37, further comprising:

issuing calibration instructions based on said analyzed reports for altering intensity and/or frequency of said emitted radiation.

39. The method of claim 37, said detecting presence and/or absence of gaseous columns further comprising:

receiving said emitted radiation in the form of a representative electrical signal in at least one band-pass filter and minimizing undesirable components of said signal;

receiving said minimized signal from said band-pass filter in at least one inverting amplifier, generating a positive amplified signal based on said received minimized signal and outputting said amplified signal;

generating an adjustable predetermined signal; and receiving said outputted amplified signal in a bubble-detect comparator circuit, comparing said outputted amplified signal with said predetermined signal to determine presence and/or absence of gas bubbles in medium, and outputting a comparison result for generating at least one said analysis report.

40. The method of claim 39, said minimizing undesirable components of said signal further comprising:

reducing noise component in said signal utilizing a high-pass filter in said band-pass filter, and outputting said reduced noise signal to a low-pass filter in said band-pass filter for further minimizing undesirable components of said signal.

41. The method of claim 37, said detecting presence and/or absence of gaseous columns further comprising:

generating an adjustable predetermined signal;

receiving said emitted radiation in the form of a representative electrical signal in a gas-column comparator subsystem; and comparing said signal with said predetermined signal to determine presence and/or absence of gaseous columns in the medium, and outputting a comparison result for generating at least one said analysis report.

42. The method of claim 30, said separating further comprising:

periodically sampling said subtracted signal utilizing at least one sampler-sample-and-hold circuit.

43. The method of claim 37, said analyzing further comprising:

interrupting the flow of operation and providing a warning upon detection of a predetermined undesirable condition in said analysis reports.

44. The method of claim 43, wherein said predetermined undesirable condition is indication of presence and/or absence of at least one gaseous bubble and/or gaseous columns in said analysis reports.

45. The method of claim 43, wherein said predetermined undesirable condition is a time-out interrupt or indication of a malfunction.

46. The method of claim 30, wherein said medium is a substantially liquid medium.

47. The method of claim 30, wherein said emitting is in frequencies of visible light.

48. The method of claim 19, said separating further comprising periodically sampling said subtracted signal utilizing at least one sampler-sample-and-hold circuit.

* * * * *